United States Patent
Canali et al.

(10) Patent No.: US 8,778,141 B2
(45) Date of Patent: Jul. 15, 2014

(54) HAND-HELD APPARATUS FOR CONTROLLING THE CONDITION OF A CIRCULATING BAND IN A PAPERMAKING MACHINE

(75) Inventors: Luca Canali, Milan (IT); Giovanni Cristini, Bergamo (IT)

(73) Assignee: S.A. Giuseppe Cristini S.p.A., Milan (IT)

(*) Notice: Subject to any disclaimer, the term of this patent is extended or adjusted under 35 U.S.C. 154(b) by 0 days.

(21) Appl. No.: 13/824,311

(22) PCT Filed: Sep. 19, 2011

(86) PCT No.: PCT/IB2011/054096
§ 371 (c)(1),
(2), (4) Date: Jul. 29, 2013

(87) PCT Pub. No.: WO2012/035521
PCT Pub. Date: Mar. 22, 2012

(65) Prior Publication Data
US 2013/0299112 A1    Nov. 14, 2013

(30) Foreign Application Priority Data
Sep. 17, 2010   (IT) .............................. MI2010A1698

(51) Int. Cl.
*D21F 7/06* (2006.01)
(52) U.S. Cl.
USPC ........... 162/263; 162/198; 162/199; 162/273; 700/127
(58) Field of Classification Search
USPC ........ 162/263, 198–199, 272; 700/127; 73/38
See application file for complete search history.

(56) References Cited

U.S. PATENT DOCUMENTS

| 3,056,281 | A | | 10/1962 | Smyth | |
|---|---|---|---|---|---|
| 5,135,615 | A | * | 8/1992 | Rokman | 162/263 |
| 5,349,845 | A | * | 9/1994 | Blom | 73/38 |
| 5,725,737 | A | * | 3/1998 | Pikulik et al. | 162/263 |
| 7,506,550 | B2 | | 3/2009 | Ulfert et al. | |
| 2005/0121161 | A1 | * | 6/2005 | Lilburn | 162/198 |
| 2011/0259085 | A1 | * | 10/2011 | Cristini | 73/38 |

FOREIGN PATENT DOCUMENTS

| EP | 1 225 270 A2 | 7/2002 |
|---|---|---|
| EP | 1 516 954 A2 | 3/2005 |

OTHER PUBLICATIONS

PCT International Search Report for PCT Counterpart Application No. PCT/IB2011/054096, 3 pgs., (Feb. 1, 2012).
PCT Written Opinion of the International Searching Authority for PCT Counterpart Application No. PCT/IB2011/054096, 5 pgs., (Feb. 1, 2012).

* cited by examiner

*Primary Examiner* — Mark Halpern
(74) *Attorney, Agent, or Firm* — Blakely, Sokoloff, Taylor & Zafman LLP

(57) ABSTRACT

The invention relates to a hand-held apparatus for controlling the condition of a circulating band in a papermaking machine; the apparatus comprises a hand-held body which carries: a moisture measuring device, equipped with at least one microwave sensor; a permeability measuring device, comprising at least one water delivery nozzle and a flowmeter associated with the nozzle; and a control unit connected to the measuring devices for processing signals coming therefrom; the body is equipped with at least one handle portion to be grasped by an operator for manually moving and maneuvering the apparatus.

15 Claims, 3 Drawing Sheets

HAND-HELD APPARATUS FOR CONTROLLING THE CONDITION OF A CIRCULATING BAND IN A PAPERMAKING MACHINE

CROSS-REFERENCE TO RELATED APPLICATIONS

This patent application is a U.S. National Phase Application under 35 U.S.C. §371 of International Application No. PCT/IB2011/054096, filed Sep. 19, 2011, entitled HAND-HELD APPARATUS FOR CONTROLLING THE CONDITION OF A CIRCULATING BAND IN A PAPERMAKING MACHINE, which claims priority to Italian Patent Application No. MI2010A001698, filed Sep. 17, 2010.

TECHNICAL FIELD

The present invention relates to a hand-held apparatus for controlling the condition of a circulating band in a papermaking machine.

BACKGROUND ART

As known, circulating bands (also called "mats") are used in traditional papermaking machines along loop-shaped paths and by means of which the paper material being formed is transported and processed.

Generally, each section of the machine has one specific type of band.

In any case, it is important to assess the conditions of the band, in addition to those of the material transported thereon, as the band physical features of moisture content and of permeability to water have repercussions on the quality of the sheet of paper.

It is known to assess the conditions of a band operating on a papermaking machine, by means of apparatuses which measure both the permeability and the moisture of the band itself, as disclosed for example in U.S. Pat. No. 7,506,550. The apparatus described in U.S. Pat. No. 7,506,550 includes some permeability and moisture measuring devices directly installed on the papermaking machine in a pre-established position along the band, and connected to a processing and control unit for continually monitoring the band.

In addition to being relatively complex, cumbersome and costly, apparatuses of this type are not hand-holdable.

Instead, U.S. Pat. No. 3,056,281 describes a hand-held apparatus for measuring the porosity of a mat used on papermaking machines.

SUMMARY

It is an object of the present invention to provide an apparatus which does not have the drawbacks herein noted from the known art; in particular, it is an object of the invention to provide an apparatus having a small volume which is simple and effective to use and which can be used manually by an operator on various parts of the papermaking machine, as well as on various machines.

Therefore, the present invention relates to a tool for simultaneously measuring moisture and permeability of a band for making the sheet of paper, as defined in basic terms in the appended claim 1, and in its additional features in the dependent claims.

The apparatus of the invention is simple and effective to use, also has a small volume and contained weight and thus is capable of being manually used by an operator, who may use the apparatus in various positions on a machine or also on various machines.

Apparatuses currently exist on the market which may measure the moisture or the permeability of a band for making the sheet of paper. However, all detections involve a certain risk, albeit limited, for the operators, which is connected to moving components and parts of the paper machine, not least, the bands themselves. Being able to detect/measure the moisture and the permeability at the same time doubles the safety of use and halves the detection times, hence thus decreasing the costs of usage.

BRIEF DESCRIPTION OF THE DRAWINGS

Further features and advantages of the present invention will become more apparent from the following description of a non-limiting embodiment thereof, with reference to the figures of the accompanying drawings, in which.

DETAILED DESCRIPTION

Figure 1:
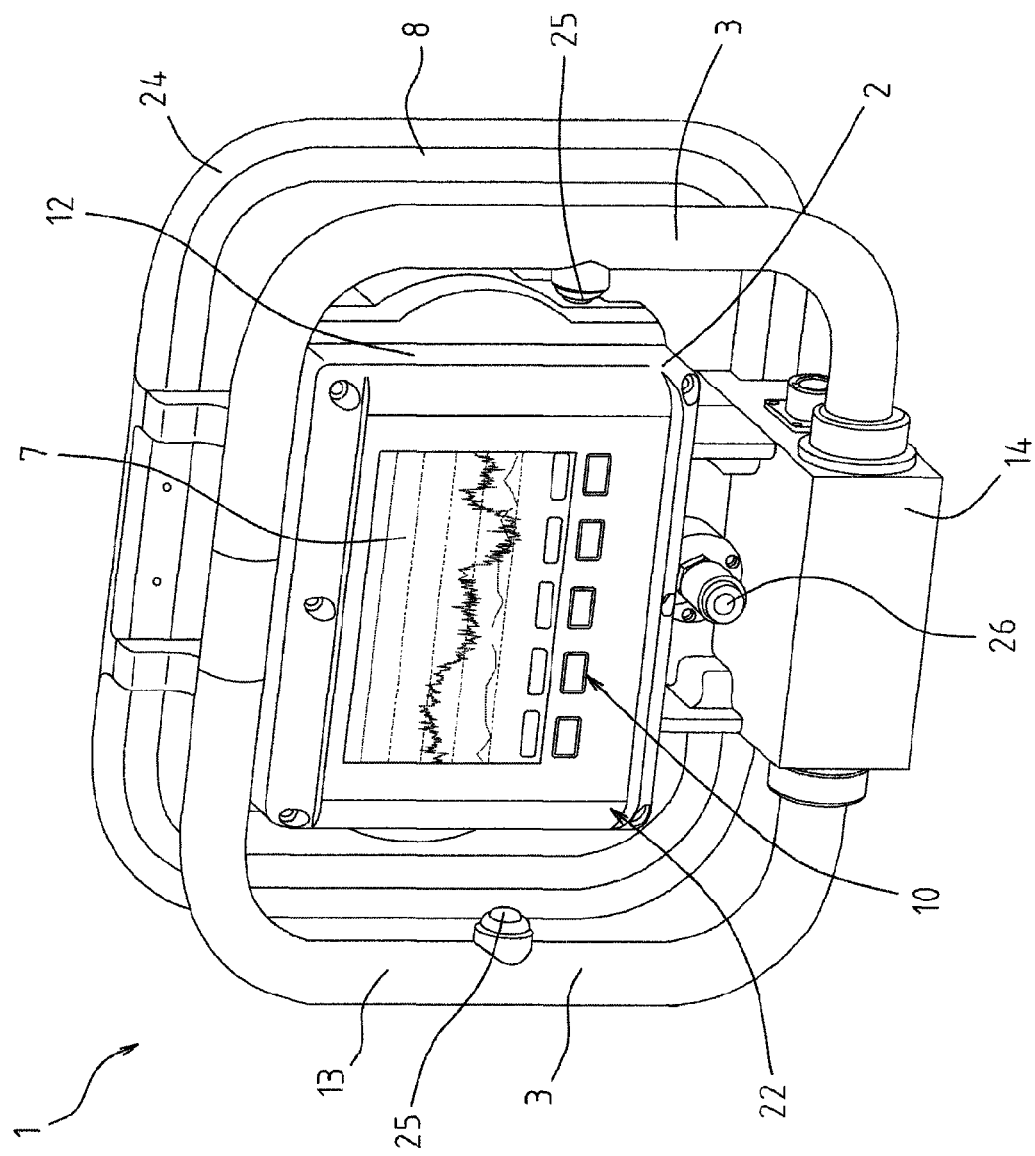
FIG. 1 is a diagrammatic and perspective front view of an apparatus in accordance with the invention.
Figure 2:
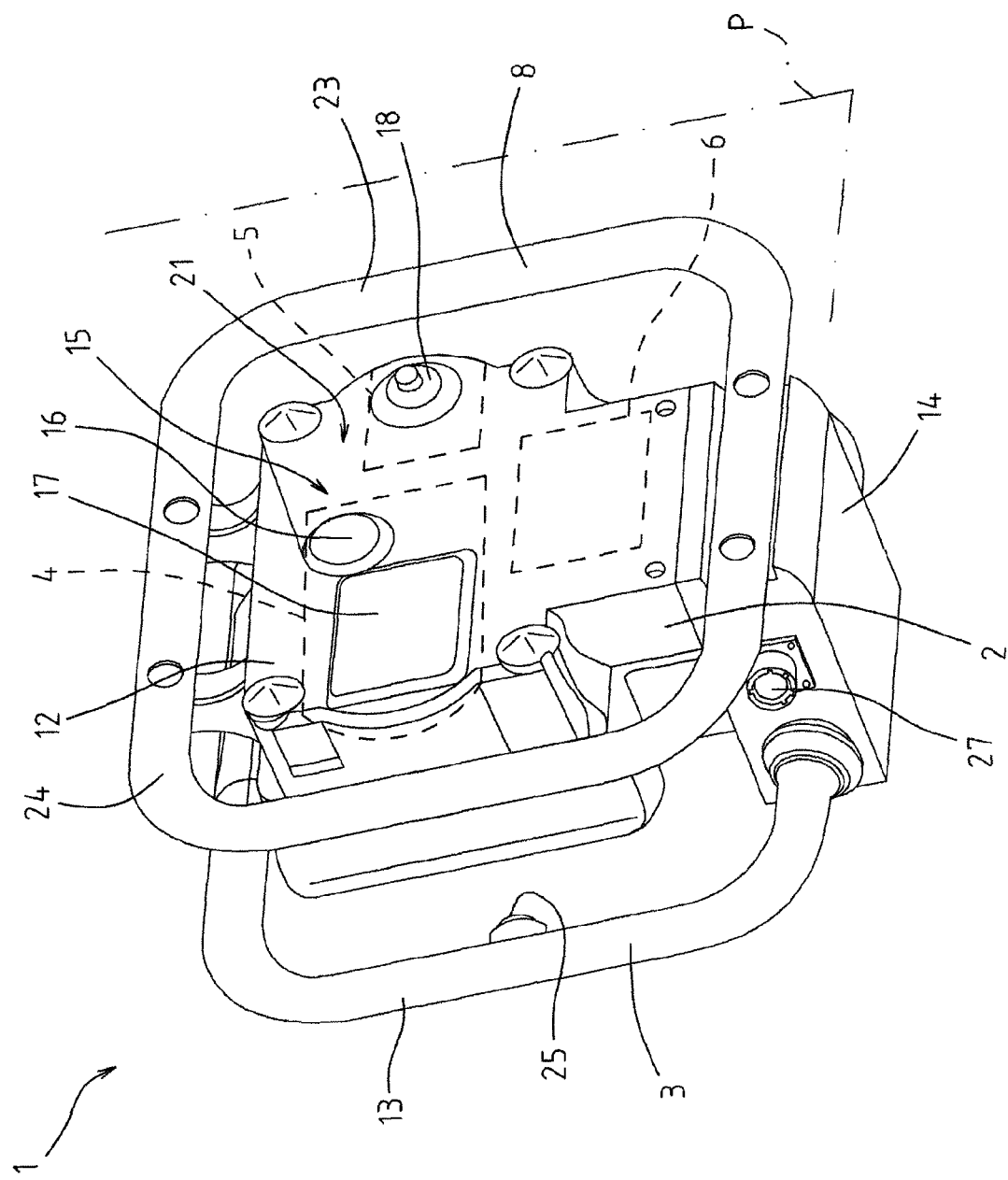
FIG. 2 is a diagrammatic and perspective rear view of the apparatus in FIG. 1.
Figure 3:
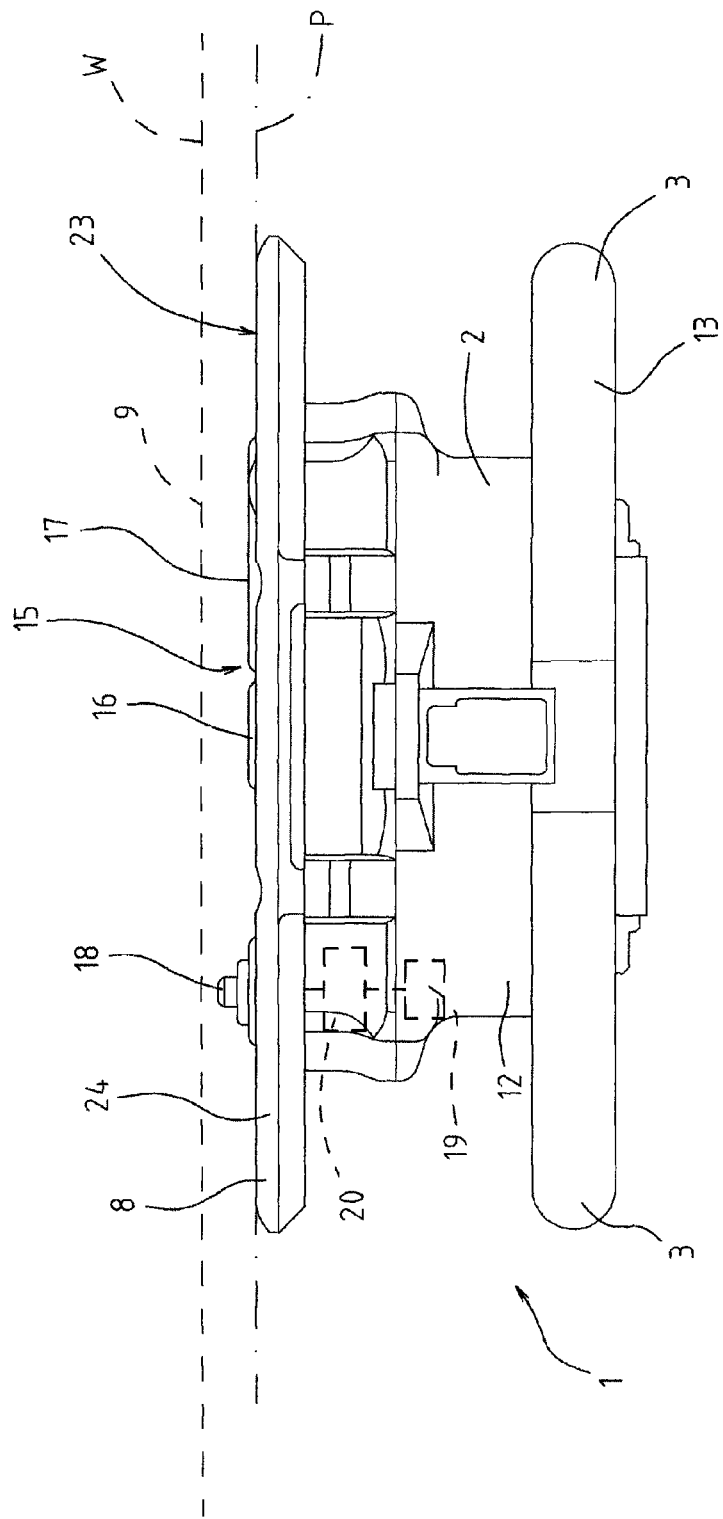
FIG. 3 is a diagrammatic side view of the apparatus in FIG. 1, shown together with a section of band for which there is the desire to assess the conditions by means of the apparatus.

Numeral 1 in the accompanying figures indicates a hand-held apparatus, as a whole, for controlling the conditions of a circulating band W (diagrammatically shown only in FIG. 3) in a papermaking machine (in particular, a mat or other processing belt operating in any section of a papermaking machine), specifically by means of permeability and moisture measurements of the band.

The term "hand-held" is intended as an apparatus having shape, sizes and weight such as to be easily moved and used by hand by an operator.

Apparatus 1 comprises a hand-held body 2, i.e. manually operable by an operator, equipped with at least one handle portion 3 which is graspable by an operator to manually move and manoeuvre apparatus 1.

Body 2 supports: a moisture measuring device 4; a permeability measuring device 5; a control unit 6 connected to measuring devices 4, 5 for processing signals coming therefrom; a display 7 connected to the control unit 6 for visualizing data processed by the control unit 6, and an abutment structure 8 intended to co-operate, in use, with a surface portion 9 of band W for which there is the desire to verify the conditions.

Display 7 may be of touch-screen type, and/or be associated with a keypad 10 by means of which the operator dialogues with the control unit 6.

In the non-limiting embodiment disclosed, body 2 comprises a casing 12, which accommodates the measuring devices 4, 5 and the control unit 6, and a handle structure 13 which projects from casing 12 and comprises at least two opposite handle portions 3 to be grasped by respective hands of the user; in particular, the two handle portions 3 project from opposite sides of an end portion 14 of casing 12; the handle portions 3 face each other from opposite sides of casing 12 and are laterally external with respect to casing 12.

In the non-limiting case disclosed, the handle structure 13 is substantially loop-shaped and the two handle portions 3 form respective lateral sections which are diametrically opposite to the loop-shaped handle structure 13.

It is understood that the handle structure 13, as well as casing 12 and in general apparatus 1 as a whole, may have different shapes from the ones herein described and shown by way of mere example.

The moisture measuring device 4 is of microwave-type, in itself substantially known, and comprises at least one microwave sensor 15; in greater detail, the microwave sensor 15 has an emitter 16 for emitting a signal which is sent to band W, and a receiver 17, for detecting a frequency response of band W; the control unit 6 processes the response received from receiver 17 and obtains a moisture value of band W therefrom.

The permeability measuring device 5 comprises a water delivering nozzle 18, a pressure controller 19 connected to nozzle 18 in such a way that nozzle 18 delivers a flow of water at preset pressure, in particular substantially constant, and a flowmeter 20 associated with nozzle 18 for measuring the amount of water which flows through nozzle 18 in the unit of time at the preset pressure (constant).

Optionally, the permeability measuring device 5 also includes a pressure sensor (not shown for simplicity) associated with nozzle 18 for detecting the pressure of the flow of water delivered by nozzle 18; such a pressure sensor is connected to the control unit 6, which considers the pressure values detected by the pressure sensor when calculating the permeability in order to compensate for any pressure deviations from the preset value.

Indeed, to obtain a more accurate and reliable permeability value, the flowmeter 20 should measure the flow which flows in nozzle 18 at constant pressure. However, since it may occur that the pressure is not exactly constant, also due to the measuring itself underway which involves a loss of pressure, the variation in pressure may be conveniently compensated to obtain a more accurate and reliable permeability value.

As already noted, the measuring devices 4, 5, as well as the control unit 6, are accommodated in casing 12. It is understood that the devices 4, 5 and/or the control unit 6 may be contained in respective separate containers, however supported by body 2 and/or connected to each other by a common support structure of body 2.

The microwave sensor 15 (more precisely, both the emitter 16 and the receiver 17) and nozzle 18 are arranged on a first face 21 of apparatus 1, in particular of casing 12; preferably, face 21 is substantially flat and emitter 16, receiver 17 and nozzle 18 project in a cantilever fashion from face 21.

Instead, display 7 is mounted on a second face 22 of apparatus 1, in particular of casing 12, opposite to the first face 21. Obviously, the faces 21, 22 must not necessarily be parallel; in particular, face 22 and/or display 7 may be tilted with respect to face 21. It is however understood that display 7 may be differently shaped, arranged and oriented with respect to that herein described and shown by mere example; for example, display 7 could be arranged on a side of apparatus 1. Display 7 could also be entirely missing and apparatus 1 could simply save the data to then send them (by cable or by means of any one wireless system, such as Wi-Fi, Bluetooth network, etc.) to an external unit (PC or other) which saves and processes them; or it could directly transmit the data (again via cable or preferably by means of a wireless system, such as Wi-Fi, Bluetooth system, etc.) to the external unit. Obviously, these connection and data transmission methods may also be provided in the presence of display 7.

The abutment structure 8 has an abutting surface 23 which defines a plane P and is shaped so as to lie, in use, on the surface portion 9 of band W and substantially keep apparatus 1 parallel to the surface portion 9 of band W (i.e. in a position in which plane P is substantially parallel to the surface portion 9).

In the example shown, the abutment structure 8 comprises a loop-shaped peripheral frame 24, for example (but not necessarily) substantially quadrilateral with rounded vertexes, arranged about and outside of casing 12 and substantially facing and parallel to the handle structure 13; frame 24 is substantially flat and has a flat front surface, opposite to the handle structure 13, which constitutes the abutting surface 23 and, in the specific case but not necessarily, is substantially an annular surface.

Advantageously, nozzle 18 projects from face 21 of apparatus 1 and protrudes out of plane P.

Optionally, the microwave sensor 15 also protrudes, with respective ends of emitter 16 and/or of receiver 17, out of plane P.

Apparatus 1 also comprises at least one switch 25 arranged on the handle portion 3 and which operates both the measuring devices 4, 5.

Preferably, as shown in the figures, apparatus 1 comprises at least two or more switches 25, each of which is arranged on one of the handle portions 3 or on keypad 10 adjacent to display 7, and operates both the measuring devices 4, 5 or individually only one thereof, in such a way that the operator may operate apparatus 1 with either one hand or the other, or with both hands. Specifically, the operator may operate both the devices 4,5 together with a single switch 25, or individually by means of respective switches 25, in such a way as to simultaneously start measuring moisture and permeability of band W.

Body 2 is then equipped with a hydraulic fitting 26 which is connectable to an external hydraulic circuit for supplying water to nozzle 18; and with a connector 27 which is connectable to a data transmission cable to connect the control unit 6 to an external computer or to another external unit (memory bank, etcetera). It is understood that the connection may also be of wireless type (Wi-Fi, Bluetooth network, etcetera); in such a case, apparatus 1 includes a suitable wireless transmission (known and not shown for simplicity).

Apparatus 1 may be equipped with batteries (accommodated in body 2, for example in casing 12) and/or with an electric power outlet (not shown).

Once the required hydraulic, and if necessary, the required electrical connections have been made, in use, the operator grasps the two handle portions 3 (or at least one of them) and brings apparatus 1 to the wanted position to perform the required measurements on band W.

Hence the operator abuts the abutment structure 8 on the surface portion 9 of band W and operates apparatus 1 by means of at least one of the switches 25; the measuring devices 4,5, which are connected to the control unit 6, measure the moisture and the permeability, respectively, of band W.

More precisely, the microwave sensor 15 emits microwaves on band W and detects the frequency response of band W, and the control unit 6 processes such a response on the basis of preset calculation algorithms, to provide moisture values (or of other parameter related to moisture) of band W. Meanwhile, nozzle 18 delivers a flow of water at preset pressure (constant) and the flowmeter 20 associated with nozzle 18 measures the amount of water which flows through nozzle 18 in the unit of time; the measurement is sent to the control unit 6 which, again on the basis of preset algorithms, obtains permeability values (or in any even related to permeability) of band W therefrom.

The control unit 6 is also capable of processing the data provided by the measuring devices 4, 5 to possibly provide further parameters which are representative of the conditions of band W, calculated according to the moisture and permeability values detected.

According to one variant, rather than it also being carried by body 2, the control unit 6 is located in remote position on another support, for example on another hand-held supporting element (such as a bracelet of the type used for so-called wrist PCs) or on a fixed support; the measuring devices 4, 5 are connected or connectable to the control unit 6, for example by cable or in wireless mode.

Although one feature of apparatus 1 is that it is manually hand-held and manoeuvrable by an operator, the compact sizes of apparatus 1 make it also usable for a substantially automated use; indeed apparatus 1 may be mounted on a movable carriage so as to be carried on band W and moved thereon without requiring the direct intervention of an operator.

For example, the carriage on which the apparatus is mounted is slidable on a track installed perpendicular or transversal to band W; the carriage moves along the track and apparatus 1 may be operated automatically.

In particular, apparatus 1 is equipped with an ignition control which starts saving the data following the beginning of data generation by the flowmeter 20 and/or by the pressure sensor, and/or by a trigger which reads the passing of the marking line which all bands have on the surface thereof.

Preferably, apparatus 1 is mounted or removably hooked on the carriage so as to be both usable manually by the operator and on the carriage.

Lastly, it is understood that further modifications and variants may be made to the apparatus herein described and shown, which do not depart from the scope of the appended claims.

What is claimed is:

1. A hand-held apparatus for controlling the condition of a circulating band in a papermaking machine, comprising a hand-held body, which is manually operable by an operator and equipped with at least one handle portion shaped to be grasped by an operator for manually moving and manoeuvring the apparatus; the body carrying a permeability measuring device; the apparatus being characterized in that the permeability measuring device comprises at least one water delivering nozzle and a flowmeter associated with the nozzle for measuring the flow of water which flows through the nozzle; and the body also carries a moisture measuring device equipped with at least one microwave sensor; the measuring devices being connected or connectable to a control unit which processes signals transmitted by the measuring devices.

2. An apparatus according to claim 1, wherein the control unit is also carried by the hand-held body, or is arranged in a remote position and receives signals from the devices by cable or in wireless mode.

3. An apparatus according to claim 1, comprising a pressure controller connected to the nozzle in such a way that the nozzle delivers a flow of water at preset pressure, in particular substantially constant; and wherein the flowmeter measures the amount of water which flows through the nozzle at the preset pressure.

4. An apparatus according to claim 1, wherein the microwave sensor has an emitter for sending a signal on the band, and a receiver for detecting a frequency response of the band from which the control unit obtains a moisture value of the band.

5. An apparatus according to claim 1, wherein the microwave sensor and the nozzle are arranged on a first face of the apparatus and the apparatus comprises a display, mounted on a second face of the apparatus, preferably opposite to the first face, for visualizing data processed by the control unit.

6. An apparatus according to claim 1, wherein the body comprises a casing which accommodates the measuring devices; and wherein at least two opposite handle portions project from opposite sides of the casing to be grasped by respective hands of the user.

7. An apparatus according to claim 1, wherein the body is equipped with a hydraulic fitting which is connectable to an external hydraulic circuit for supplying water to the nozzle.

8. An apparatus according to claim 1, and equipped with a connector which is connectable to a data transmission cable, and/or with a wireless transmission, for connecting the control unit to a computer or other type of external units.

9. An apparatus according to claim 1, comprising at least one switch arranged on the handle portion and which operates both the measuring devices.

10. An apparatus according to claim 1, and comprising two switches each of which operates both the measuring devices; the switches being arranged on respective handle portions to be grasped by respective hands of an operator in such a way that the operator may operate the apparatus with either one hand or the other or with both hands.

11. An apparatus according to claim 1, and comprising an abutment structure, having an abutting surface which defines a plane and is shaped so as to lie, in use, on a surface portion of the band and substantially keep said plane parallel to the surface portion of the band.

12. An apparatus according to claim 11, wherein the abutment structure comprises a peripheral frame arranged about a casing which accommodates the measuring devices.

13. An apparatus according to claim 12, wherein the frame is loop-shaped.

14. An apparatus according to claim 11, wherein at least the nozzle, and optionally also at least one end of the microwave sensor, projects from a face of the apparatus and protrudes out of the plane defined by the abutment structure.

15. An apparatus according to claim 1, wherein the measuring devices are contained in respective separate containers, both supported by the body and/or connected to each other by a common support structure.

* * * * *